United States Patent
Suon et al.

(10) Patent No.: US 7,041,117 B2
(45) Date of Patent: *May 9, 2006

(54) RETRIEVAL DEVICES FOR VENA CAVA FILTER

(75) Inventors: Naroun Suon, Lawrence, MA (US); James Weldon, Roslindale, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/789,110

(22) Filed: Feb. 26, 2004

(65) Prior Publication Data

US 2004/0172042 A1    Sep. 2, 2004

Related U.S. Application Data

(63) Continuation of application No. 10/020,705, filed on Dec. 14, 2001, now Pat. No. 6,726,621, which is a continuation of application No. 09/404,116, filed on Sep. 23, 1999, now Pat. No. 6,342,062.

(60) Provisional application No. 60/101,616, filed on Sep. 24, 1998.

(51) Int. Cl.
 *A61M 29/00* (2006.01)
(52) U.S. Cl. ............. 606/200; 606/108; 606/194; 606/195
(58) Field of Classification Search ........... 606/106, 606/108, 194, 195, 198, 200
See application file for complete search history.

(56) References Cited

U.S. PATENT DOCUMENTS

| | | | |
|---|---|---|---|
| 3,952,747 A | 4/1976 | Kimmell, Jr. | |
| 4,425,908 A | 1/1984 | Simon | |
| 4,643,184 A | 2/1987 | Mobin-Uddin | |
| 4,781,177 A * | 11/1988 | Lebigot | 128/897 |
| 4,817,600 A * | 4/1989 | Herms et al. | 606/198 |
| 4,832,055 A | 5/1989 | Palestrant | |
| 4,990,156 A | 2/1991 | Lefebvre | |
| 4,994,079 A | 2/1991 | Genese et al. | |
| 5,108,406 A | 4/1992 | Lee | |
| 5,147,379 A | 9/1992 | Sabbaghian et al. | |
| 5,152,777 A * | 10/1992 | Goldberg et al. | 606/200 |
| 5,171,233 A | 12/1992 | Amplatz et al. | |
| 5,171,314 A | 12/1992 | Dulebohn | |
| 5,300,086 A | 4/1994 | Gory et al. | |
| 5,324,304 A | 6/1994 | Rasmussen | |
| 5,344,427 A | 9/1994 | Cottenceau et al. | |
| 5,370,657 A | 12/1994 | Irie | |
| 5,383,887 A | 1/1995 | Nadal | |

(Continued)

OTHER PUBLICATIONS

Greenfield et al., "Staging of Fixation and Retrievability of Greenfield Filters", *Journal of Vascular Surgery*, pp. 744-750, Nov. 1994.

(Continued)

*Primary Examiner*—Glenn K Dawson
*Assistant Examiner*—Michael G Mendoza
(74) *Attorney, Agent, or Firm*—Crompton, Seager & Tufte LLC

(57) ABSTRACT

A device for removing a thrombus filter from a blood vessel is disclosed. A device in accordance with the present invention includes a shaft having a proximal end, a distal end, and a lumen extending therethrough, a wire having a first end and a second end, the wire being partially disposed within the lumen of the shaft, a portion of the wire extending beyond the distal end of the shaft and forming a loop, and a portion of the wire extending beyond the proximal end of the shaft.

3 Claims, 3 Drawing Sheets

U.S. PATENT DOCUMENTS

| | | |
|---|---|---|
| 5,413,586 A | 5/1995 | Dibie et al. |
| 5,415,630 A | 5/1995 | Gory et al. |
| 5,626,605 A * | 5/1997 | Irie et al. .................. 623/1.1 |
| 5,634,942 A | 6/1997 | Chevillon et al. |
| 5,649,953 A | 7/1997 | Lefebvre |
| 5,681,347 A | 10/1997 | Cathcart et al. |
| 5,944,728 A | 8/1999 | Bates |
| 5,968,071 A * | 10/1999 | Chevillon et al. .......... 606/200 |
| 5,993,474 A | 11/1999 | Ouchi |
| 6,007,558 A | 12/1999 | Ravenscroft et al. |
| 6,251,122 B1 | 6/2001 | Tsukernik |
| 6,258,026 B1 | 7/2001 | Ravenscroft et al. |
| 6,331,183 B1 | 12/2001 | Suon |
| 6,342,062 B1 | 1/2002 | Suon et al. |
| 6,447,530 B1 | 9/2002 | Ostrovsky et al. |
| 6,569,183 B1 * | 5/2003 | Kim et al. .................. 606/200 |
| 6,726,621 B1 | 4/2004 | Suon et al. |

OTHER PUBLICATIONS

Millward, "Temporary and Retrievable Inferior Vena Cava Filters: Current Status[1]" *JVIR*, vol. 9, No. 3, pp. 381-387, May-Jun. 1998.

"Gunther Tulip Vena Cava Filter Set", brochure, 10 pgs.

"Tricep™ Hooked-Prong Grasping Forceps", Microvasive Boston Scientific Corporation brochure, 1 pg.

* cited by examiner

RETRIEVAL DEVICES FOR VENA CAVA FILTER

CROSS REFERENCE TO RELATED APPLICATION

This application is a continuation application of U.S. application Ser. No. 10,020,705 filed Dec. 14, 2001 now U.S. Pat. No. 6,726,621, which in turn is a continuation application of U.S. application Ser. No. 09/404,116 filed Sep. 23, 1999, now U.S. Pat. No. 6,342,062 issued Jan. 29, 2002, which claims the benefit of U.S. Provisional Application Ser. No. 60/101,616 filed Sep. 24, 1998.

BACKGROUND OF THE INVENTION

The present invention pertains to the field of intra vena cava filters. In particular, the present invention pertains to the retrieval of intra vena cava filters.

Intra vena cava filters are commonly implanted either temporarily or permanently in patients at risk for blood clotting.

SUMMARY OF THE INVENTION

The present invention pertains to an intra vena cava filter implantable temporarily or permanently, and methods for removal thereof. The filter includes struts having sharpened tips which engage the wall of the vein or inner surface of another organ to provide positional stability of the filter. The method in accordance with the present invention preferably includes the steps of further stabilizing the filter, compressing the struts and shielding the sharpened tips of the struts for subsequent removal of the filter.

DETAILED OF THE DESCRIPTION

Figure 1:
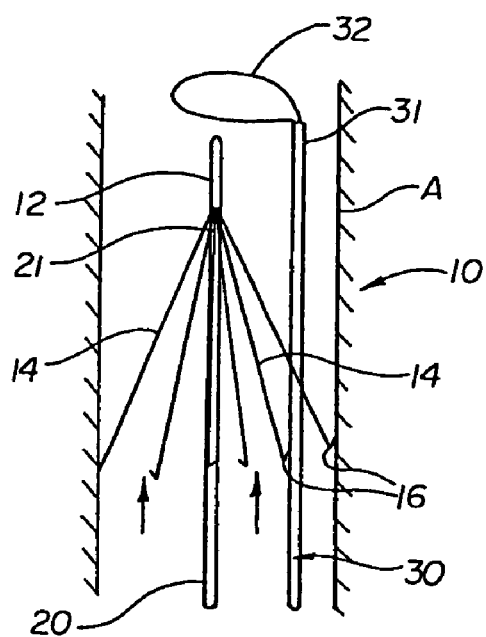
FIG. 1 is a view of an intra vena cava filter and a removal device disposed within a vessel.

Referring now to the drawings wherein like reference numerals refer to like elements throughout the several views, FIG. 1 is a side view of a filter 10 disposed within a vessel or vena cava A. Filter 10 includes a hub 12 from which extends a plurality of struts 14. Each strut preferably includes bends along its length to catch thrombus which flows through vessel A in the direction of the arrows. The end of each strut preferably includes a barb 16 for engagement with the vessel wall to stabilize filter 10 within vessel A. In particular, filter 10 can be a prior art filter such as the Greenfield™ filter made by Medi-Tech (Watertown, Mass.). Filter 10 can be placed within vessel A by way of a jugular vein access, point or other intravascular route as known to those skilled in the art.

It is anticipated that the filter disclosed herein can be placed permanently in the vena cava or other organ, as well as being placed temporarily. The tools and methods for removing the filter disclosed herein would likely be used within several weeks after implantation of the filter prior to endothelial growth over a portion of the filter making removal substantially more difficult.

Also shown in FIG. 1 is a stabilizer 20. Stabilizer 20 includes a proximal end and a distal end 21. Stabilizer 20 can be advanced to filter 10 by way of a femoral vein access point. Stabilizer 20 is preferably made from a substantially rigid biocompatible material such as, for example, a stainless steel hypotube or steerable catheter.

Disposed adjacent filter 10 in FIG. 1 is a removal device 30. Removal device 30, like stabilizer 20, can be advanced to filter 10 by way of a femoral vein access point. Removal device 30 preferably includes an elongate shaft having a proximal end (not shown) and a distal end. Shaft 30 is preferably formed from a substantially rigid, biocompatible material such as a stainless steel hypotube. Extending from the distal end of shaft 31 is a wire loop 32. Wire loop 32 is preferably formed from a NiTi alloy such as Nitinol. The wire forming loop 32 preferably extends through shaft 31 to its proximal end such that a physician can draw loop 32 into shaft 31. The wire forming loop 32 is preferably heat set or mechanically biased to bend approximately perpendicularly to shaft 31, as shown in FIG. 1, as it is advanced from the distal end of shaft 31 in vessel A.

Figure 2:
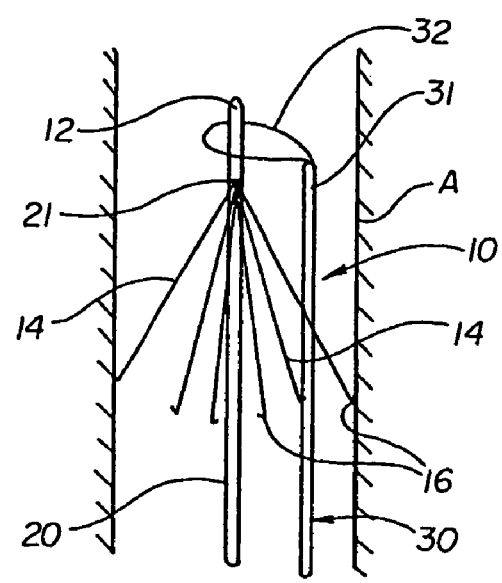
FIG. 2 is a view of the filter of FIG. 1 and the removal device in a subsequent position in the process of removal.
Figure 3:
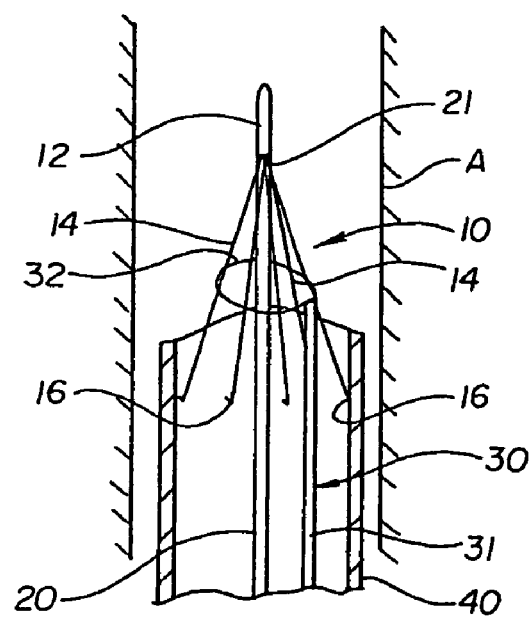
FIG. 3 is a view of the filter of FIG. 1 and the removal device in a position subsequent to that shown in FIG. 2 in the process of removal.

FIG. 2 is a view of the filter of FIG. 1, wherein loop 32 has been placed around filter 10 by pulling removal device 30 proximally. FIG. 3 is a view of filter 10 of FIG. 1, wherein device 30 has been pulled yet more proximally than shown in FIG. 2, relative to filter 10 and stabilizer 20. By pulling removal device 30 more proximally as shown in FIG. 3, struts 14 are compressed inwardly toward stabilizer 20 such that barbs 16 are withdrawn from the wall of vessel A.

Also shown in FIG. 3, in cross section, is a removal sheath 40. Sheath 40 can be formed of a biocompatible material in a manner similar to, for example, a guide catheter. Sheath 40 can be advanced to filter 10 by way of, for example, a femoral vein access point. As can be seen in FIG. 3, once struts 14 have been compressed sufficiently inward by removal device 30, filter 10 can be withdrawn into sheath 40, and subsequently removed from the patient.

Figure 4:
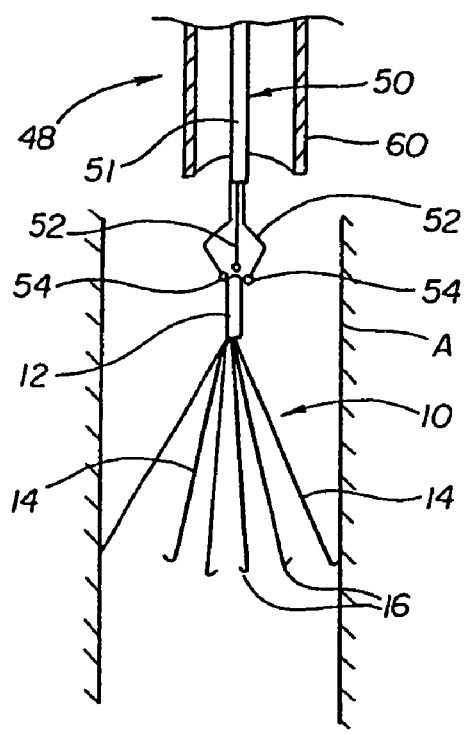
FIG. 4 is a view of the intra vena cava filter of FIG. 1 and an alternate embodiment of a removal device disposed within a vessel.

FIG. 4 is a view of the filter of FIG. 1. A removal device 48 is disposed above filter 10 in FIG. 4. Device 48 includes a stabilizer 50 and a catheter 60. Catheter 60 could be made in a manner similar to a guide catheter. Stabilizer 50 preferably includes a tubular shaft 51 having a proximal end (not shown) and a distal end. Preferably extending between the proximal end and the distal end are elongate members 52 having a distal end extending beyond the distal end of shaft 51. The distal end of members 52 are preferably bent to form a claw as shown. Atraumatic balls 54 can be disposed at the distal end of members 52. Removal device 48 can be placed in the position shown by way of, for example, a jugular vein access point.

Figure 5:
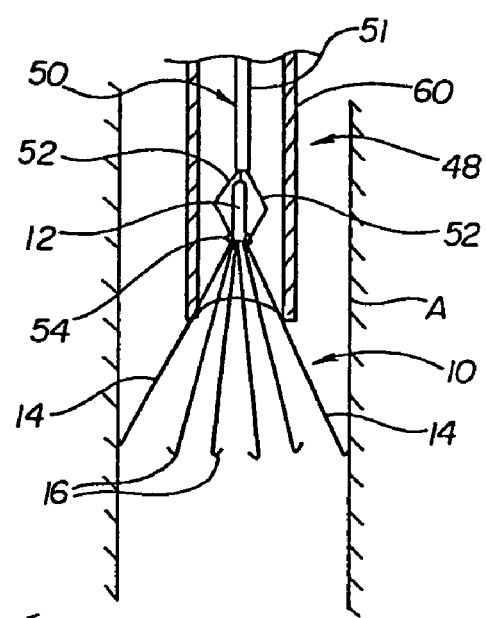
FIG. 5 is a view of the filter of FIG. 4 and the removal device in a subsequent position in the process of removal.

FIG. 5 is a view of the filter of FIG. 4 in which the claw portion of stabilizer 50 has been brought into contact with hub 12. Atraumatic balls 54 are shown engaging a portion of hub 12 to hold filter 10. The claw portion of device 50 can be closed to grasp hub 12 by advancing shaft 51 over members 52 to engage the claw portion forcing balls 54 toward each other. Once filter 10 is grasped by stabilizer 50, catheter 60 can be advanced into engagement with struts 14.

Figure 6:
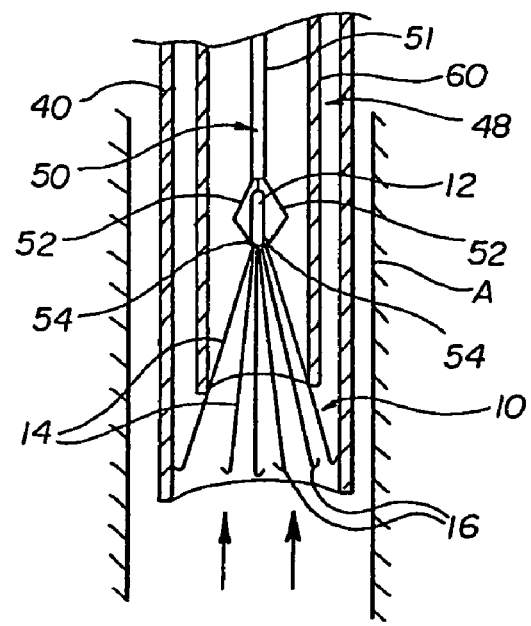
FIG. 6 is a view of the filter of FIG. 4 and the removal device in a position subsequent to that shown in FIG. 5 in the process of removal.

FIG. 6 shows the filter, of FIG. 4, wherein catheter 60 has been advanced further than as shown in FIG. 5, to compress struts 14 inwardly and draw tips 16 away from the wall of vessel A Sheath 40 has been advanced from, for example, a jugular vein access point over the entire filter 10. Sheath 40 shields the vessel wall from tips 16 during subsequent removal of filter 10 in the direction shown by the arrows.

Figure 7:
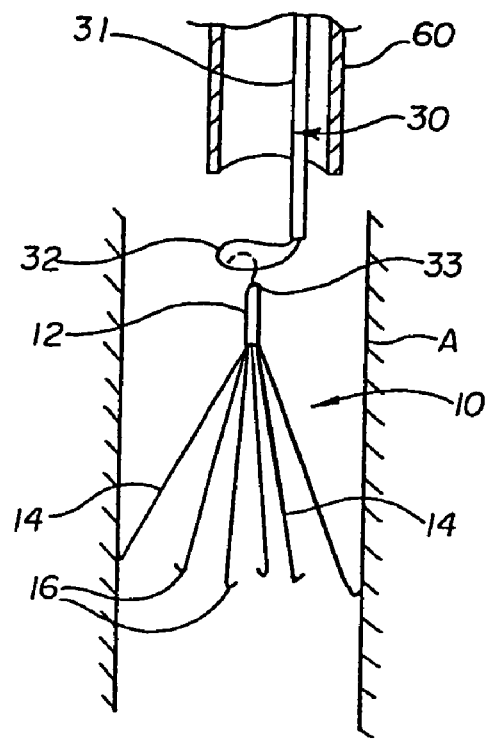
FIG. 7 is a view of the intra vena cava filter of FIG. 1 and yet an alternate embodiment of a removal device disposed within a vessel.

FIG. 7 is a view of the filter of FIG. 1 disposed in vena cava A. Positioned above filter 10 is removal device 30 disposed within catheter 60. Device 30 and catheter 60 are preferably advanced into-this position by way of a jugular vein access point.

Figure 8:
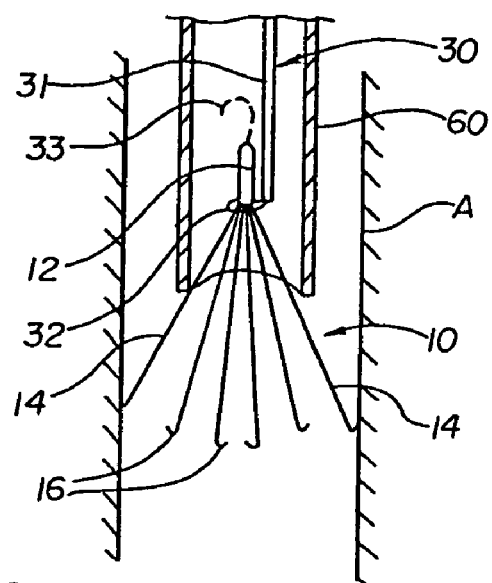
FIG. 8 is a view of the filter of FIG. 7 and the removal device in a subsequent position in the process of removal.

As shown in FIG. 8, loop 32 of device 30 has been placed around a portion of hub 12. Alternatively, hub 12-could include a hook 33 shown in phantom lines, to which loop 32 could be attached. The wire forming loop 32 has been drawn proximally into shaft 31 to tighten loop 32 around hub 12. Catheter 36 has been advanced distally to engage struts 14.

Figure 9:
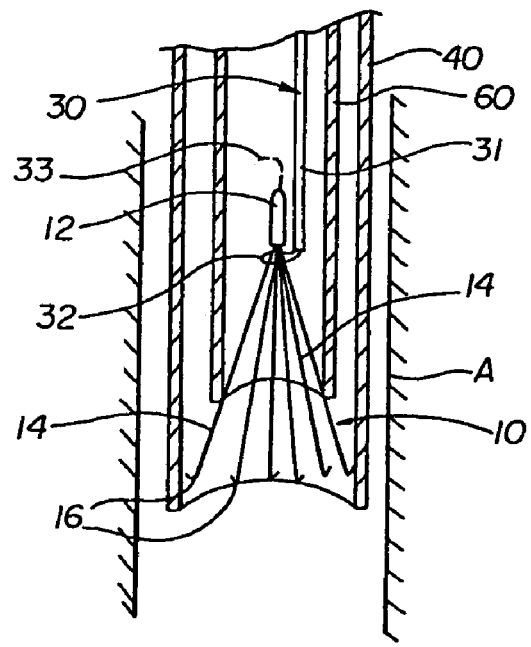
FIG. 9 is a view of the filter of FIG. 1 and the removal device in a position subsequent to that shown in FIG. 8 in the process of removal.

As shown in FIG. 9, catheter 60 has been advanced further relative to device 30 and filter 10 than as shown in FIG. 8. By advancing catheter 60 in this way, struts 14 have been compressed inwardly to disengage tips 16 from the wall of vessel A. Embodiments of the present invention have been envisioned, in which loop 30 is adapted to compress struts 14 inward and disengage tips 16 from the wall of vessel A. Methods in accordance with the present invention have been envisioned in which loop 32 is advanced distally to compress struts 14 inward and disengage tips 16 from the wall of vessel A. Sheath 40 is advanced distally as shown in FIG. 9 to cover filter 10 and shield the vessel wall from tip 16 as filter 10 is subsequently removed.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method for retrieving a vena cava filter from a blood vessel, comprising the steps of:
    providing a vena cava filter retrieval device, the device including a tubular sheath, a shaft slidable within the sheath, and means for retrieving a filtering device attached to the shaft;
    advancing the retrieval device through a blood vessel to a location adjacent a vena cava filter, the vena cava filter including a hub, the hub defining a narrow portion of the filter, and a plurality of arms extending from the hub, the arms defining a wide portion of the filter;
    extending the shaft out from a distal end of the sheath so that the means for retrieving a filtering device engages the narrow portion;
    retracting the filter into the sheath; and
    wherein means for retrieving a filtering device includes a plurality of distal members and wherein the step of extending the shaft out from a distal end of the sheath so that the means for retrieving a filtering device engages the hub includes engaging the distal members with the hub.

2. A method for retrieving a vena can filter from a blood vessel, comprising the steps of:
    providing a vena cava filter retrieval device, the device including a tubular sheath, a shaft slidable within the sheath, and means for retrieving a filtering device attached to the shaft;
    advancing the retrieval device through a blood vessel to a location adjacent a vena cava filter, the vena cava filter including a hub, the hub defining a narrow portion of the filter, and a plurality of arms extending from the hub, the arms defining a wide portion of the filter, each arm including a barb at a proximal end thereof that is embedded within the blood vessel;
    extending the shall out from a distal end of the sheath so that the means for retrieving a filtering device engages the narrow portion;
    releasing the barbs from the blood vessel;
    retrieving the filter into the sheath; and
    wherein means for retrieving a filtering device includes a plurality of distal members and wherein the step of extending the shaft out from a distal end of the sheath so that the means for retrieving a filtering device engages the hub includes engaging the distal members with the hub.

3. A method for releasing a vena cava filter from a blood vessel, comprising the steps of:
    providing a vena cava filter retrieval device, the device including a tubular sheath and a retrieval member slidable disposed within the sheath;
    advancing the retrieval device through a blood vessel to a location adjacent a vena cava filter, the vena cava filter including a hub, the hub defining a narrow portion of the filter, and a plurality of arms extending from the hub, the arms defining a wide portion of the filter, each arm including a barb at a proximal end thereof that is embedded within the blood vessel;
    engaging the retrieval member with the narrow portion so that the barbs release from the blood vessel; and
    wherein the retrieval member includes a plurality of distal members and wherein the step of engaging the retrieval member with the hub so that the barbs release from the blood vessel includes engaging the distal members with the hub.

* * * * *

UNITED STATES PATENT AND TRADEMARK OFFICE
CERTIFICATE OF CORRECTION

| | |
|---|---|
| PATENT NO. | : 7,041,117 B2 |
| APPLICATION NO. | : 10/789110 |
| DATED | : May 9, 2006 |
| INVENTOR(S) | : Naroun Suon and James Weldon |

It is certified that error appears in the above-identified patent and that said Letters Patent is hereby corrected as shown below:

Claim 2, Col. 4 line 13, delete "can", and add --cava--

Claim 2, Col. 4 line 26, delete "shall", and add --shaft--

Claim 3, Col. 4 line 41, delete "slidable", and add --slidably--

Signed and Sealed this

Twenty-sixth Day of December, 2006

JON W. DUDAS
*Director of the United States Patent and Trademark Office*